United States Patent
McElroy et al.

(10) Patent No.: US 11,944,476 B2
(45) Date of Patent: Apr. 2, 2024

(54) APPARATUS AND METHOD OF ASSEMBLY OF MODULE FOR A CT DETECTOR

(71) Applicant: Minfound Medical Systems Co. Ltd., Hangzhou (CN)

(72) Inventors: Mark McElroy, Akron, OH (US); Zhiyuan Zha, Macedonia, OH (US)

(73) Assignee: MINFOUND MEDICAL SYSTEMS CO., LTD., Hangzhou (CN)

( * ) Notice: Subject to any disclaimer, the term of this patent is extended or adjusted under 35 U.S.C. 154(b) by 520 days.

(21) Appl. No.: 17/237,605

(22) Filed: Apr. 22, 2021

(65) Prior Publication Data

US 2022/0338825 A1    Oct. 27, 2022

(51) Int. Cl.
*A61B 6/00*  (2006.01)
*A61B 6/03*  (2006.01)
*A61B 6/42*  (2024.01)

(52) U.S. Cl.
CPC ............ *A61B 6/4411* (2013.01); *A61B 6/035* (2013.01); *A61B 6/4291* (2013.01); *Y10T 29/49002* (2015.01)

(58) Field of Classification Search
CPC .......... A61B 6/4411; A61B 2090/3762; A61B 2090/374; A61N 5/0613; G01T 1/20182; Y10T 29/49002
USPC ................................ 29/592.1, 428, 434, 467
See application file for complete search history.

(56) References Cited

U.S. PATENT DOCUMENTS

| | | | |
|---|---|---|---|
| 8,824,635 B2 | 9/2014 | Tkaczyk et al. | |
| 8,831,180 B2 | 9/2014 | Hsieh et al. | |
| 9,285,489 B2 | 3/2016 | Couture et al. | |
| 2012/0087462 A1* | 4/2012 | Ikhlef | G21K 1/025 378/4 |
| 2012/0170710 A1* | 7/2012 | Niedzielski | A61G 13/126 5/601 |
| 2012/0183119 A1 | 7/2012 | Ikhlef et al. | |
| 2020/0000422 A1 | 1/2020 | Yu et al. | |

FOREIGN PATENT DOCUMENTS

| | | |
|---|---|---|
| DE | 102012100267 A1 | 7/2012 |
| EP | 1387185 A1 | 2/2004 |

* cited by examiner

*Primary Examiner* — Thiem D Phan
(74) *Attorney, Agent, or Firm* — Fishman Stewart PLLC

(57) ABSTRACT

A fixture for fabricating a detector mini-module includes a lower block having a Y-datum lower block upper surface, an X-datum lower block surface, and a Z-datum lower block surface orthogonal to both the Y-datum lower and X-datum block surface surfaces. A mount block for a detector is positionable and in contact with the X-datum lower block surface, the Y-datum lower block upper surface, and the Z-datum lower block surface. An intermediate block is positionable on the lower block having an aperture passing through an upper surface and having an X-datum intermediate block surface and a Z-datum intermediate block surface. When a mount block for the detector mini-module is positioned on the lower block, the mount block is biased having an X-axis mount block planar surface aligned with the X-datum lower block surface, and biased having a Z-axis mount block planar surface aligned with the Z-datum lower block surface.

18 Claims, 12 Drawing Sheets

APPARATUS AND METHOD OF ASSEMBLY OF MODULE FOR A CT DETECTOR

TECHNICAL FIELD

This disclosure relates generally to diagnostic imaging and, more particularly, to an apparatus and method of assembling a module for a CT detector.

BACKGROUND

Typically, in computed tomography (CT) imaging systems, a rotatable gantry includes an x-ray tube, detector, data acquisition system (DAS), and other components that rotate about a patient table that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into visible light photons within the scintillator, and then to electrical signals within the photodiode. The electrical signals are digitized and then received and processed within the DAS. The processed signals are transmitted via a slipring (from the rotational side to the stationary side) to a computer for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Third generation multi-slices CT scanners typically include detectors having scintillator/photodiodes arrays. These detectors are positioned in an arc where the focal spot is the center of the corresponding circle. These detectors generally have scintillation crystal/photodiode arrays, where the scintillation crystal absorbs x-rays and converts the absorbed energy into visible light. A photodiode is used to convert the light to an electric current. The reading is typically linear to the total energy absorbed in the scintillator.

Typically, CT systems obtain raw data and then reconstruct images using various known pre-processing and post-processing steps to generate a final reconstructed image. That is, CT systems may be calibrated to account for x-ray source spectral properties, detector response, and other features, to include temperature. Raw x-ray data are pre-processed using known steps that include offset correction, reference normalization, and air calibration steps, as examples.

In recent years, the development of volumetric or cone-beam CT technology has led to an increase in the number of slices used in CT detectors for computed tomography systems. The detector technology used in large coverage CT enables greater coverage in patient scanning by increasing the area exposed, by using back-illuminated photodiodes. A typical detector includes an array of 16, 32, or 64 slices. However, the need for cardiac imaging has become of greater interest to enable imaging of the heart within one rotation of the detector, substantially increasing the width of the detector in the Z-axis (e.g., along the patient length), leading to a detector having 256 or more slices. Because it is impractical to build very large modules in monolithic structure to cover this number of slices and this width in the Z-axis, due to manufacturing cost and reliability concerns, smaller modules (mini-modules) are built along the Z-axis and placed along the Z-axis to build the overall length of 256 or more slices.

However, due to tight mechanical fitting requirements and the optical nature of assembly (i.e., using cameras and other optics), placement accuracy of the smaller mini-modules can be a challenge. For instance, placement of components relative to one another can be achieved by movement along X and Z axes of a detector, but such placement may not account for or address tolerance stack-up of components in the Y-axis as well. Further, using optical and mechanical placement of components by physically offsetting the components during assembly, and based on optical feedback of positions of pieces relative to one another, can itself be challenging and time consuming, and fraught with the potential for error due to subjective positioning of components (such as based on an operator who may place components based on visual location of components relative to one another).

Thus, there is a need to improve assembly procedures of mini-modules in CT detectors.

BRIEF DESCRIPTION

Embodiments are directed toward an apparatus and method of assembling a mini-module for a CT detector.

A fixture for fabricating a detector mini-module to control component positioning in 3-space coordinates along an X-axis, a Y-axis, and a Z-axis, includes a lower block. The lower block includes a Y-datum lower block upper surface, an X-datum lower block surface that is orthogonal to the Y-datum lower block upper surface, and a Z-datum lower block surface that is orthogonal to both the Y-datum lower block upper surface and the X-datum lower block surface, wherein a mount block for a detector is positionable and in contact with the X-datum lower block surface, the Y-datum lower block upper surface, and the Z-datum lower block surface. An intermediate block is positionable on the lower block having an aperture passing through an upper surface and having an X-datum intermediate block surface and a Z-datum intermediate block surface. When a mount block for the detector mini-module is positioned on the lower block, the mount block is biased having an X-axis mount block planar surface aligned with the X-datum lower block surface, and biased having a Z-axis mount block planar surface aligned with the Z-datum lower block surface.

A method of fabricating a detector mini-module to control component positioning in 3-space coordinates along an X-axis, a Y-axis, and a Z-axis, includes obtaining a lower block that includes a Y-datum lower block upper surface, an X-datum lower block surface that is orthogonal to the Y-datum lower block upper surface, and a Z-datum lower block surface that is orthogonal to both the Y-datum lower block upper surface and the X-datum lower block surface, positioning a mount block for a detector in contact with the X-datum lower block surface, the Y-datum lower block upper surface, and the Z-datum lower block surface, and positioning an intermediate block on the lower block having, the intermediate block having an aperture passing through an upper surface and having an X-datum intermediate block surface and a Z-datum intermediate block surface. When a mount block for the detector mini-module is positioned on the lower block, the mount block is biased having an X-axis mount block planar surface aligned with the X-datum lower block surface, and biased having a Z-axis mount block planar surface aligned with the Z-datum lower block surface.

Various other features and advantages will be made apparent from the following detailed description and the drawings.

DETAILED DESCRIPTION

The operating environment of disclosed embodiments is described with respect to a 128/256/512-slice computed tomography (CT) system. Embodiments are described with respect to a "third generation" CT scanner, however it is contemplated that the disclosed embodiments are applicable to other imaging systems as well, and for CT systems having more or less than the illustrated sixteen-slice system.

Figure 1:
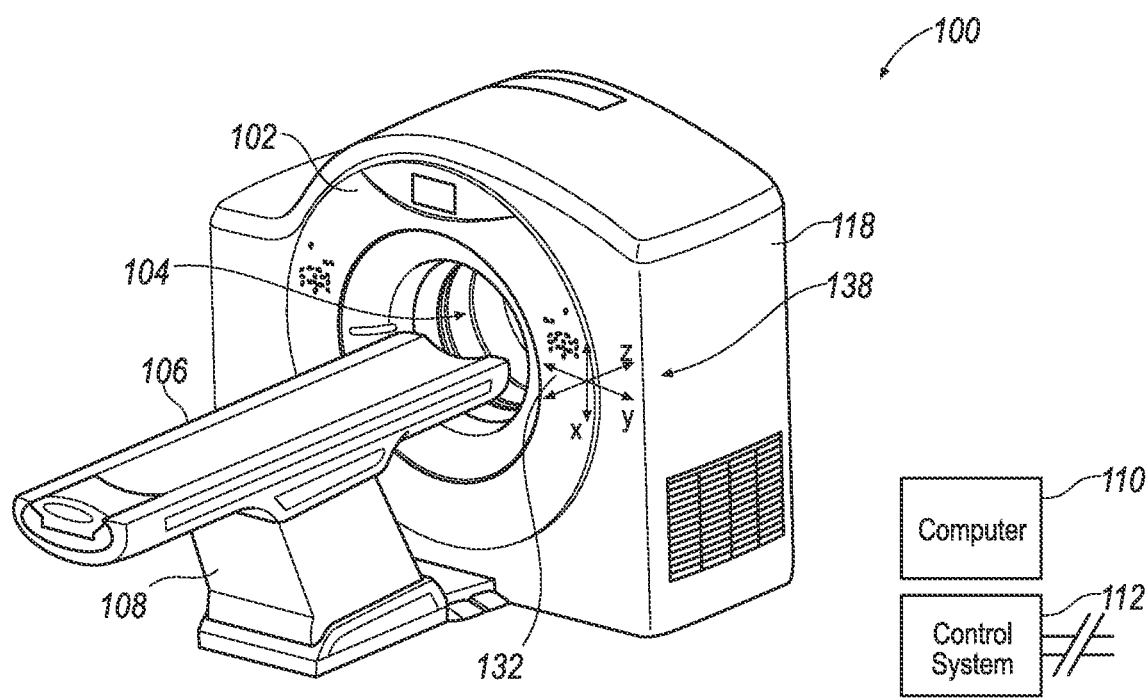
FIG. 1 is a perspective view of a CT imaging system.
Figure 2:
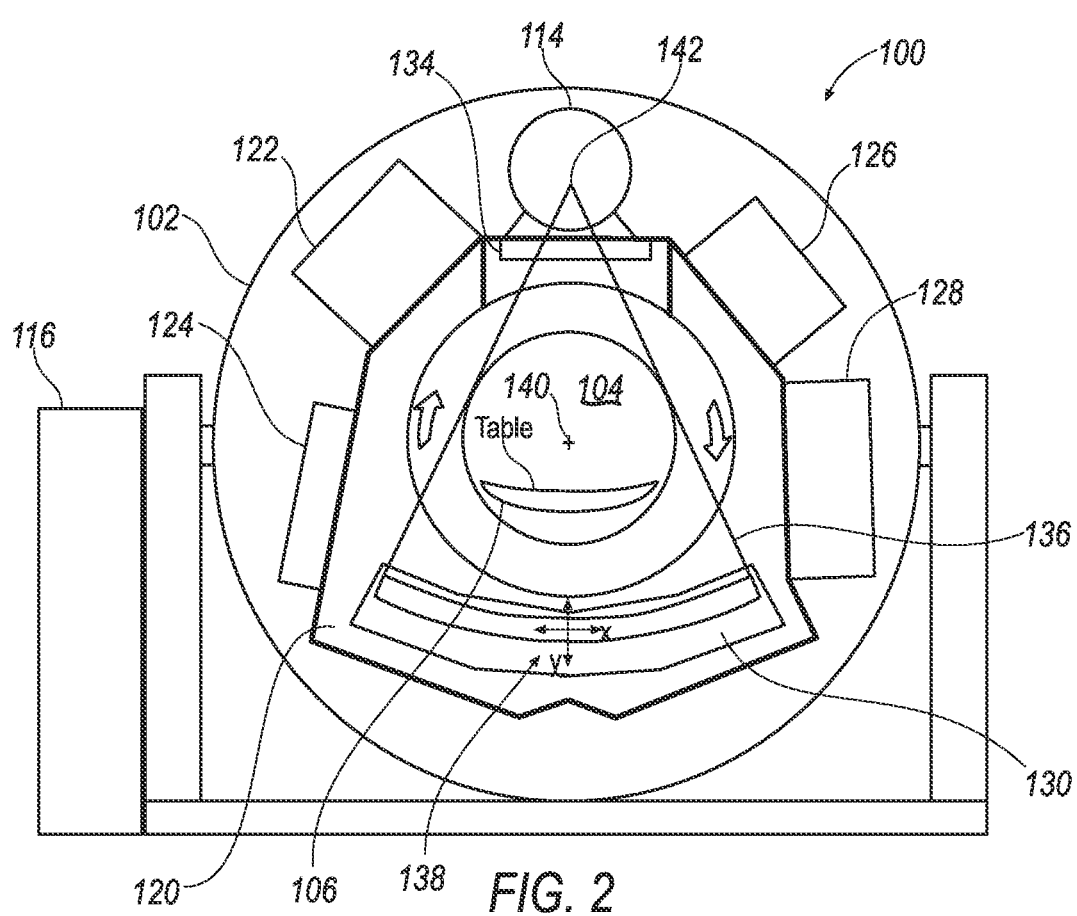
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction algorithms, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is caused to rotate about the patient up to typically a few Hz in rotational speed or more, and table 106 is caused to move the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals that are digitized and passed to DAS 124, and then to computer 110 where the data is further processed to generate an image. The imaging data may be stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and a gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
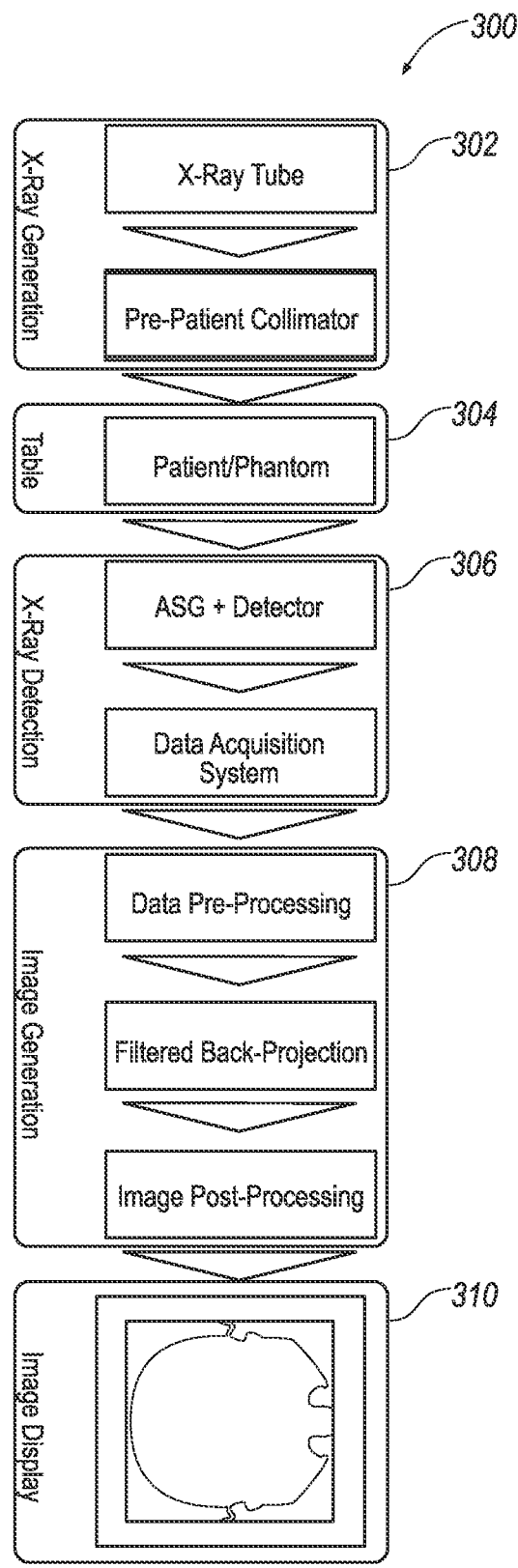
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which time table 106 passes 304 through opening 104 of gantry 102. In one example table 106 may have a patient thereon, and in another example a phantom may be used for calibration purposes.

X-ray detection 306 occurs when x-rays having emitted from x-ray tube 114 pass to detector assembly 130. An anti-scatter grid (ASG) prevents x-ray scatter (emitting for example from the patient as secondary x-rays and in a direction that is oblique to x-ray beam 136), by generally passing x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
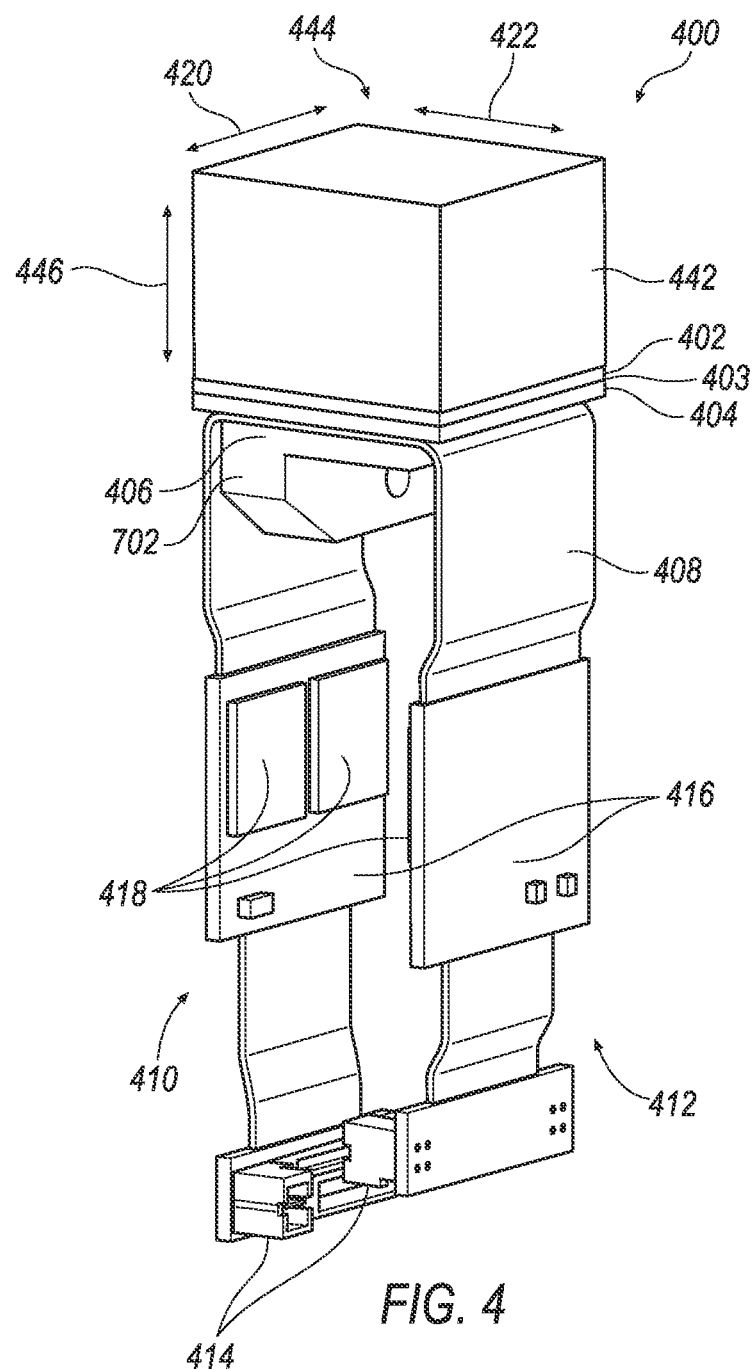
FIG. 4 illustrates a module or mini-module having a collimator attached thereto.

FIG. 4 illustrates a mini-module 400 having been assembled according to the disclosure. Mini-module 400 includes a grid of pixelated scintillators or scintillating array 402 positioned on a substrate 404, having a photodiode 403 therebetween. An alignment block or support structure 406 mechanically supports mini-module 400. Positioned between support structure 406 and substrate 404 is a flex circuit 408, which wraps within mini-module 400 and includes a first end 410 and a second end 412. Each end 410, 412 includes electrical connectors 414, a circuit board or electronics package 416, ASIC or processors 418, and other associated electronic components (not shown). Mini-module 400, when placed on a gantry of a CT system, such as system 100 above, in one example has an orientation of a Z or slice direction 420 and an X or channel direction 422.

An anti-scatter grid 442 having a plurality of plates 444 is positioned on an upper surface of scintillating array 402. In the example shown, anti-scatter grid 442 is a monolithic device having plates that extend in X or channel direction 422, or may have plates that extend in both X or channel direction 422, as we as Z or slice direction 420. Anti-scatter grid 442 in the illustrated example may be fabricated using a plurality of tungsten plates, or as another example may be fabricated using 3D printing technology and having high density materials such as tungsten or other x-ray absorbing materials therein. Accordingly, in one example, anti-scatter grid 442 is a two-dimensional (2D) collimator with plates 444 spaced from one another having a spacing that corresponds with a spacing of pixels.

Plates 444 may thereby be fabricated in anti-scatter grid 442 to be slightly non-parallel to one another so that each may be directed and approximately aimed toward a focal spot of a CT system. For instance, referring to FIG. 2, mini-modules 400 may be positioned accordingly within CT detector assembly 130 and on gantry 102, having each plate 444 extending along a length and in a direction 446 such that, when CT detector 130 is positioned in CT system 100, the length of plates 444 extend 446 approximately toward focal spot 142 of CT system 100.

Figure 5:
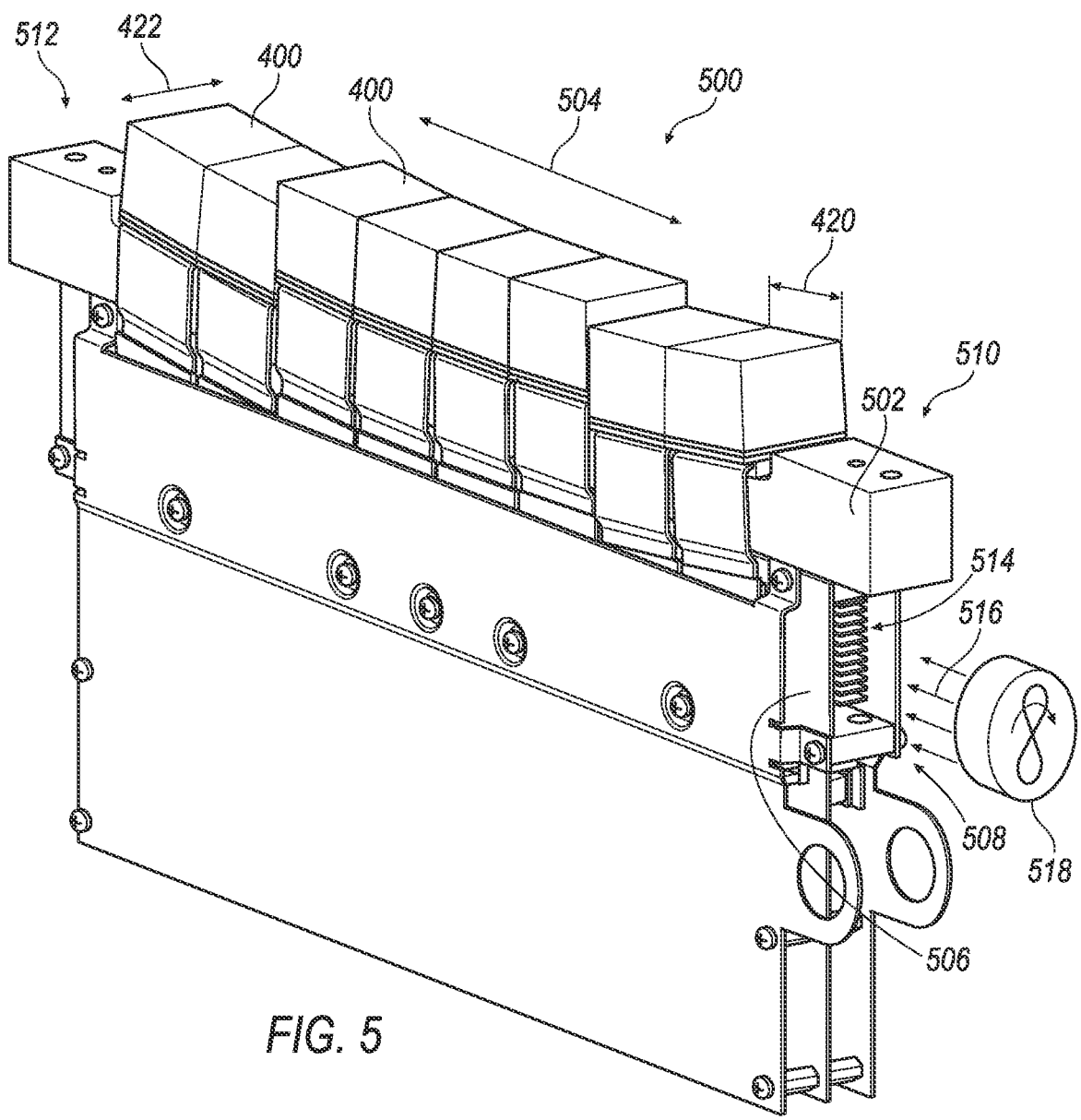
FIG. 5 a detector sub-assembly having a plurality of mini-modules.

Referring now to FIG. 5, a detector sub-assembly (module) 500 shows a plurality of mini-modules 400, being positioned on an alignment block 502. As shown, each mini-module 400 includes Z or slice direction 420, which combine to provide a composite coverage in a system Z direction 504, which corresponds with triad 138 in FIGS. 1 and 2. Correspondingly, each mini-module 400 includes X or channel direction 422, and modules 400 are thereby combined or stacked side-by-side to form a plurality of detectors, corresponding with triad 138 of FIGS. 1 and 2, forming detector assembly 130. Thus, according to the disclosure, each mini-module 400 is fabricated in the fashion described herein. As such, global system tolerances do not accumulate, such as if all plates 444 were placed with respect to alignment block 502, for example. In addition, each mini-module 400 may be classified and placed within the detector according to the measured quality of the modules.

Referring still to FIG. 5, a detector assembly or sub-assembly 500 shows a plurality of mini-modules 400, being positioned on an alignment block 502. As shown, each mini-module 400 includes Z or slice direction 420, which combine to provide a composite coverage in a system Z direction 504, which corresponds with triad 138 in FIGS. 1 and 2. Correspondingly, each mini-module 400 includes X or channel direction 422, and modules 400 are thereby combined or stacked side-by-side to form a plurality of detectors, corresponding with triad 138 of FIGS. 1 and 2, forming detector assembly 130.

Thus, according to the disclosure, a detector assembly 500 for CT system 100 includes plurality of detector mini-modules 400, each detector module including a grid of pixelated scintillators 402, a reflector (as is commonly known), a photodiode 403 having pixelations that correspond with the pixelated scintillators 402, and an electronics package 416 for processing acquired X-ray data. A support structure 502, corresponding with support structure 406 above, extends along Z-direction 504 of CT system 100 and includes plurality of detector mini-modules 400 positioned thereon. A heat sink 506 extends along Z-direction 504 and includes support structure 502 mounted thereon. Heat sink 504 includes a passageway 508 passing therethrough and along Z-direction 504, such that cooling air may pass into passageway 508 at a first end 510 of heat sink 506 and exit passageway 508 at a second end 512 of heat sink 506 opposite first end 510. Heat sink 506 includes a plurality of fins or plates 514 positioned within passageway 508 and are thermally coupled to heat sink 506, each of plurality of plates 508 extending along Z-direction 504. As such, air or another cooling medium 516 is blown into passageway 508 via a fan, as an example, represented by element 518 in FIG. 5.

Figure 6:
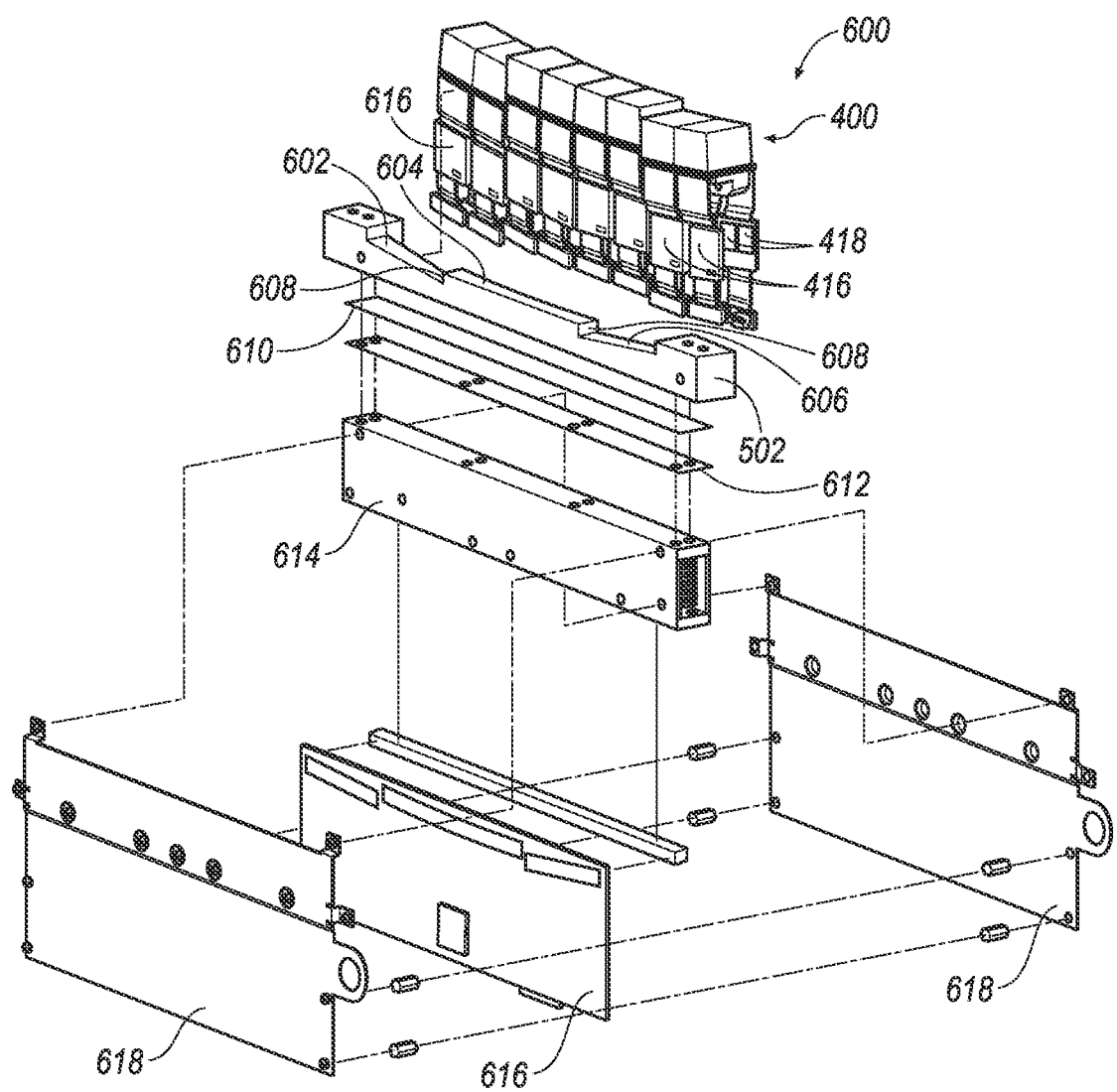
FIG. 6 illustrates an exploded and perspective view that includes the detector sub-assembly of FIG. 5.

Referring to FIG. 6, an exploded and perspective view 600 of detector assembly 500 is shown. Modules, or mini-modules 400 are shown proximate one another, and proximate support structure 502. Support structure 502 includes surfaces 602, 604, 606 which include steps 608. And, surfaces 602, 604, 606 may themselves include non-parallel surfaces such that each individual mini-module 400 may be directly aimed toward focal spot 142, regardless of which step it is positioned on.

Also, according to the disclosure detector assembly 500 includes a heater 610 and a thermal barrier 612. Detector assembly 500 includes a heat sink 614, a FPGA printed circuit board 616, and support plates 618. As known in the art, thermal control is an important aspect of detector design, and thus heater 610 uniformly heats support structure 502, thereby maintaining each of mini-modules 400 at uniform temperature during calibration and use. Thermal barrier 612 reduces the propensity for heat to flow from ASIC or processors 418 on each of circuit board or electronics package 416. Heat sink 614 is thermally coupled to each circuit board or electronics package 416, preventing heat from flowing to support structure 502 to negatively affect thermal calibration or performance of the detectors.

Figure 7:
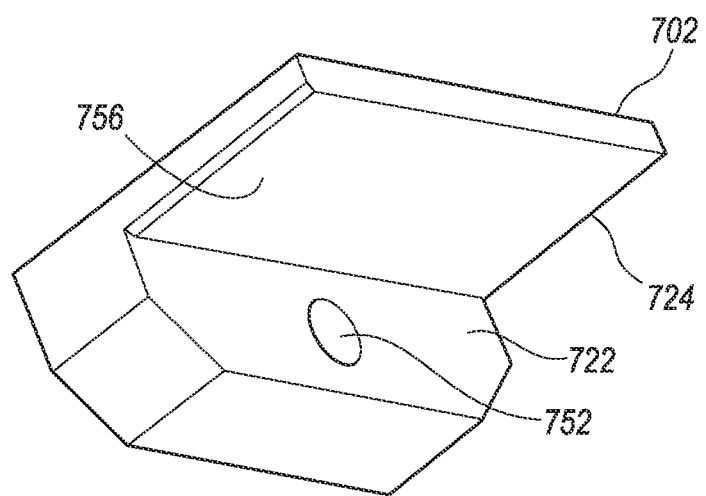
FIG. 7 illustrates a mount block.
Figure 13:
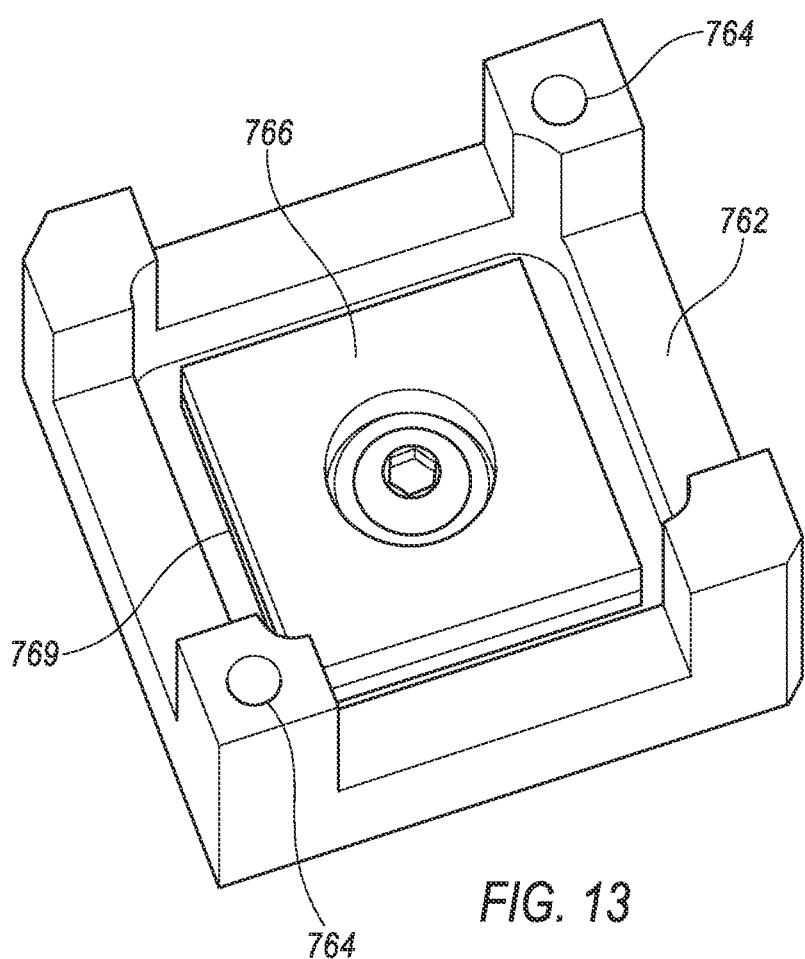
FIG. 13 illustrates an upper block.
Figure 14:
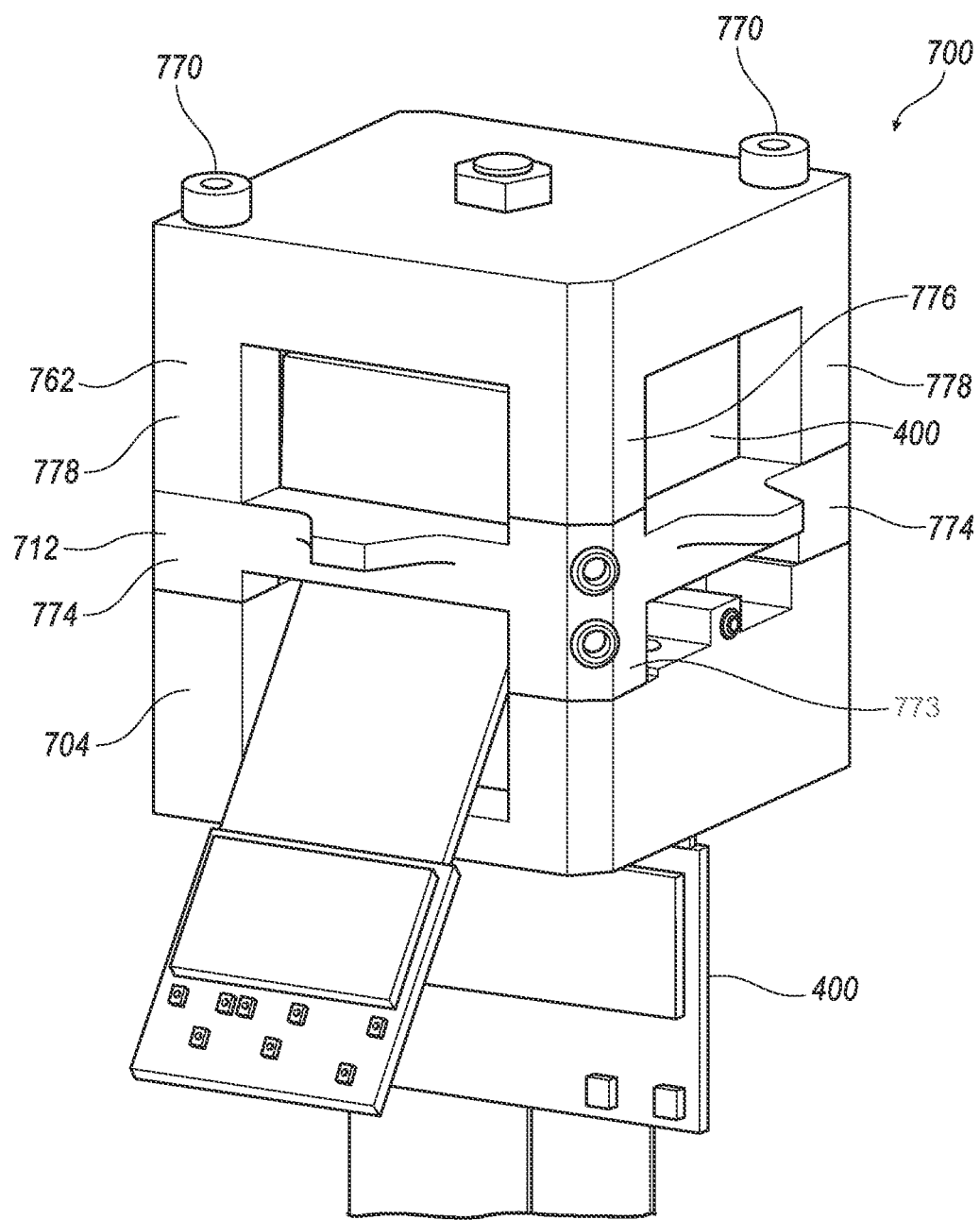
FIG. 14 illustrates a full assembly of the disclosed fixture, assembled with the mini-module therein.

Referring now to FIGS. 7-14, mini-modules 400 are assembled according to the disclosure using a fixture 700 as shown assembled in FIG. 14, having a mini-module 400 therein. Fixture 700 for fabricating detector mini-module 400 controls component positioning in 3-space coordinates along an X-axis, a Y-axis, and a Z-axis. FIG. 7 illustrates a mount block 702 for detector mini-module 400, as also illustrated in FIG. 4. Mount block 702 includes various references surfaces that are interactive with surfaces of fixture 700 according to the disclosure and as described herein.

Figure 8:
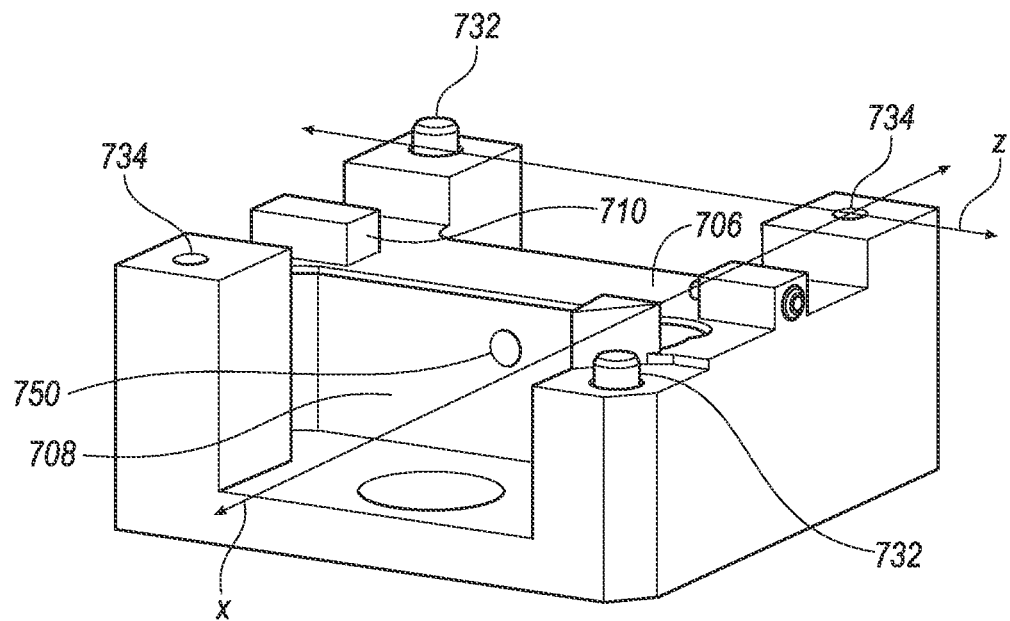
FIG. 8 illustrates a lower block.
Figure 9:
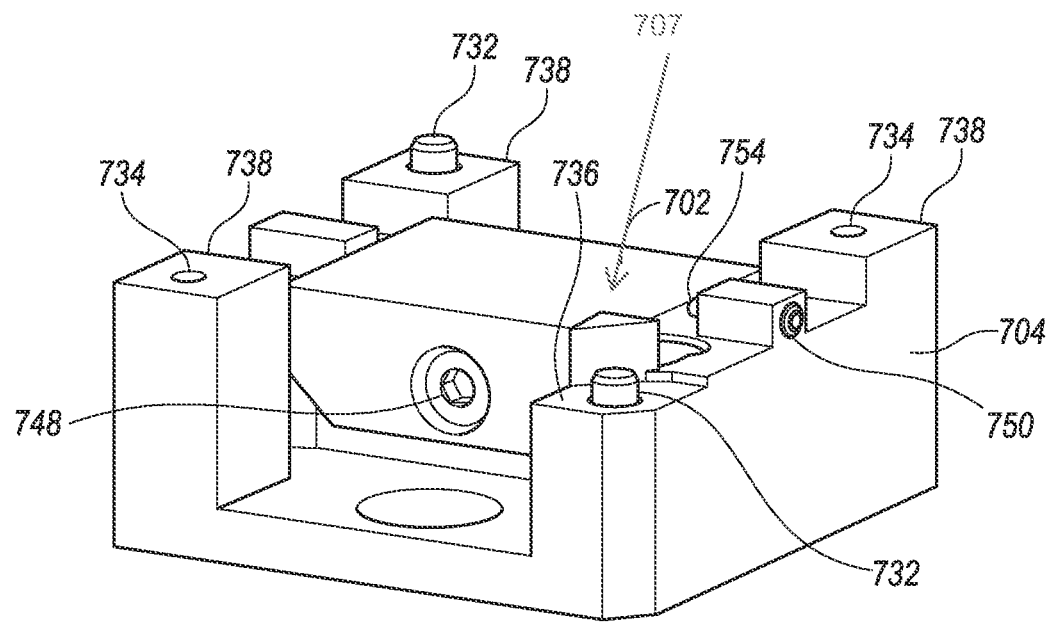
FIG. 9 illustrates the lower block with the mount block positioned therein.
Figure 10:
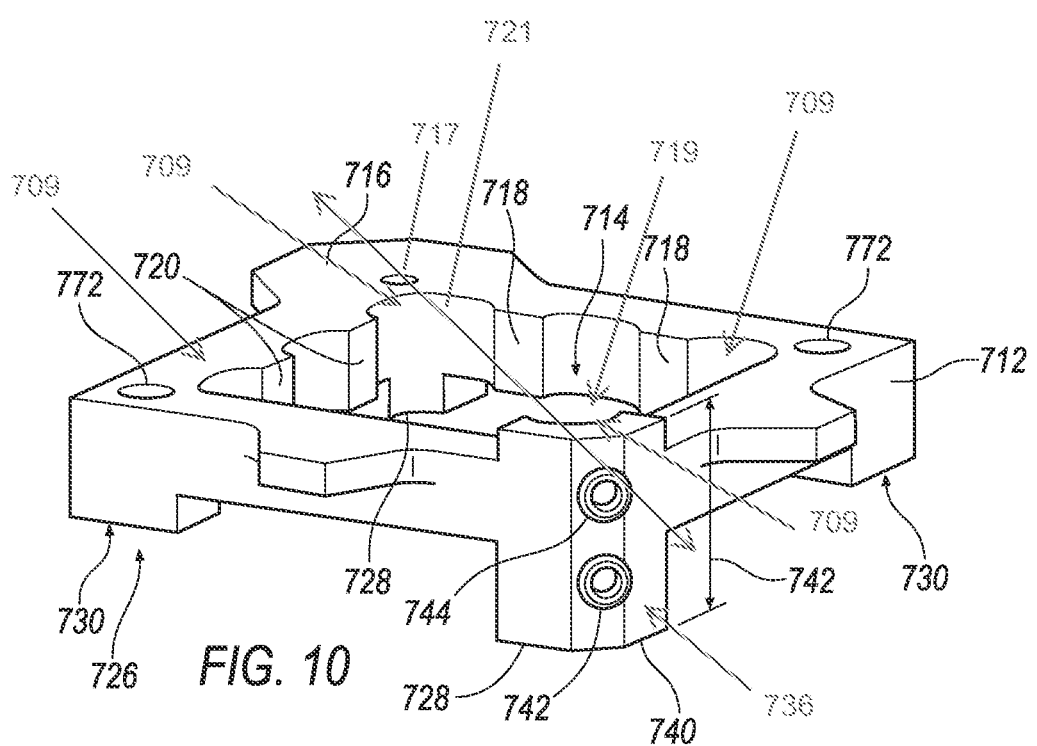
FIG. 10 illustrates an intermediate block.

Fixture 700 includes a lower block 704, shown in FIG. 8, and having mount block 702 positioned thereon in FIG. 9. FIG. 8 shows references datums X and Z, which correspond with those of triad 138 in other figures. Lower block 704 includes a Y-datum lower block upper surface 706, an and X-datum lower block surface 708 that is orthogonal to the Y-datum lower block upper surface 706. Lower block 704 includes a Z-datum lower block surface 710 that is orthogonal to both Y-datum lower block upper surface 706 and X-datum lower block surface 708. Mount block 702 is positionable and in contact with X-datum lower block surface 708, Y-datum lower block upper surface 706, and Z-datum lower block surface 710. An intermediate block 712, shown in FIG. 10, is positionable on lower block 704 and having an aperture 714 passing through an upper surface 716 and having one or more X-datum intermediate block surfaces 718, and having one or more Z-datum intermediate block surfaces 720. When mount block 702 for detector mini-module 400 is positioned on lower block 704, mount block 702 is biased having an X-axis mount block planar surface 722 aligned with X-datum lower block surface 708, and biased having a Z-axis mount block planar surface 724 aligned with Z-datum lower block surface 710. Thus, mount block 702 is L-shaped, having a portion of the L-shape extending along the Y-axis, and mount block 702 is biased having X-axis mount block planar surface 722 positioned against X-datum lower block surface 708 using a fastener passing through an aperture in the portion of the lower block.

Referring to FIGS. 8 and 9, a pair of holes 734 are positioned at two corners opposite one another, and a pair of nubs or dowl-ends 732 are positioned at the other two corners of lower block 704. Referring to FIG. 10, a matching pair of holes 772 are positioned that correspond with holes 734, and a second pair of apertures 717/719 are positioned that correspond with nubs 732. In the illustration, apertures 717/719 are positioned along a diagonal 721 that passes through centers of apertures 717/719. Aperture 719, in one example (not visible in the perspective view of FIG. 10), is a circular hole, and aperture 717 is an oblong or slotted hole that extends along diagonal 721. Thus, when intermediate block 712 is positioned on lower block 704, holes 772 align with holes 734, and referenced with respect to one another by fitting one of nubs 732 in FIGS. 8 and 9 (in the foreground of the perspective view) with aperture 719, and the other nub 732 (toward the back in the perspective view) with aperture 717. Aperture 717, being oblong or slotted, thereby provides tolerance along diagonal 721 such that alignment in both X and Z is effected, while allowing for any tolerance mis-match between the locations of nubs 732 and apertures 717/719.

Figure 11:
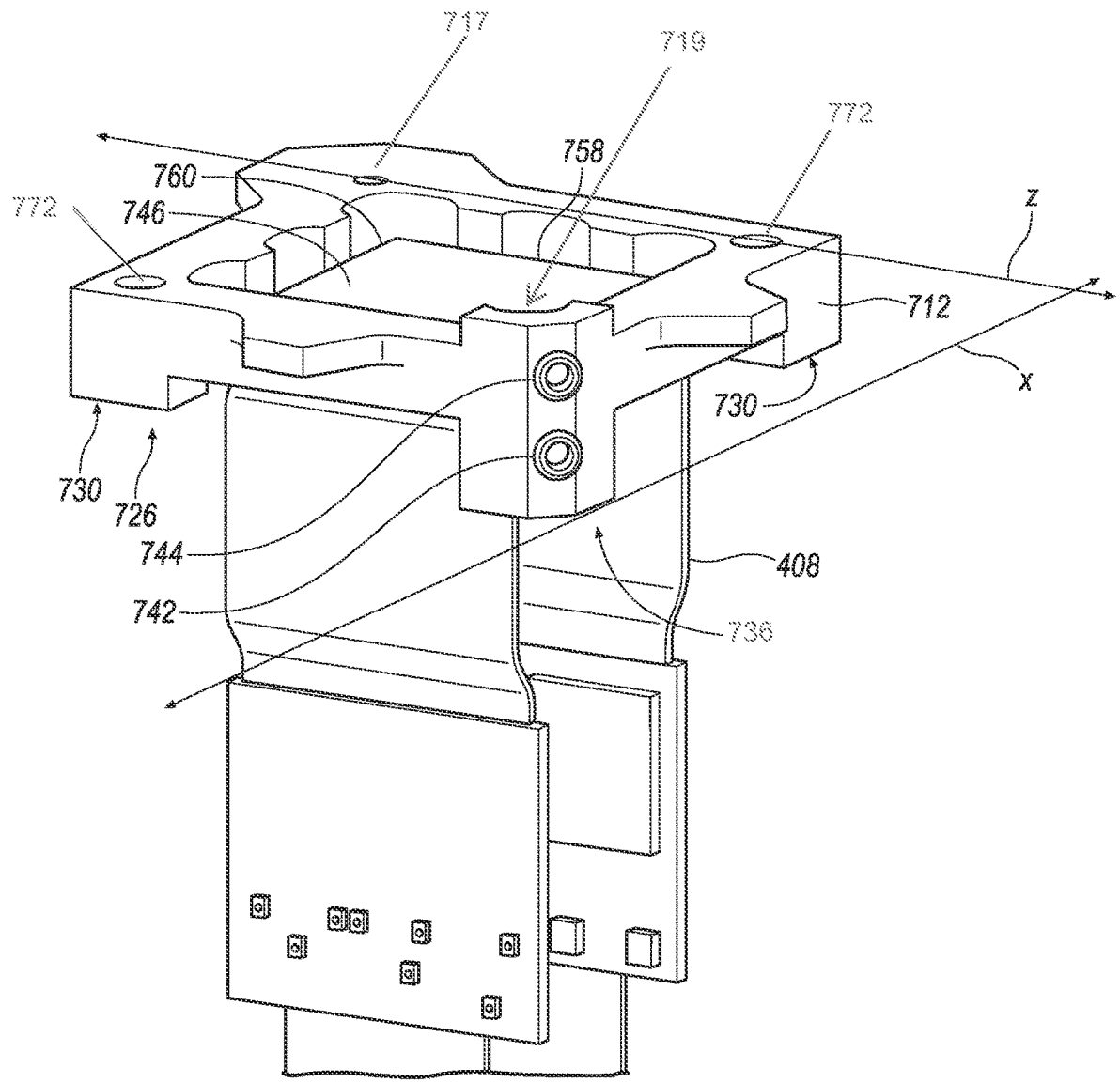
FIG. 11 illustrates a flex or PCB positioned in the intermediate block.
Figure 12:
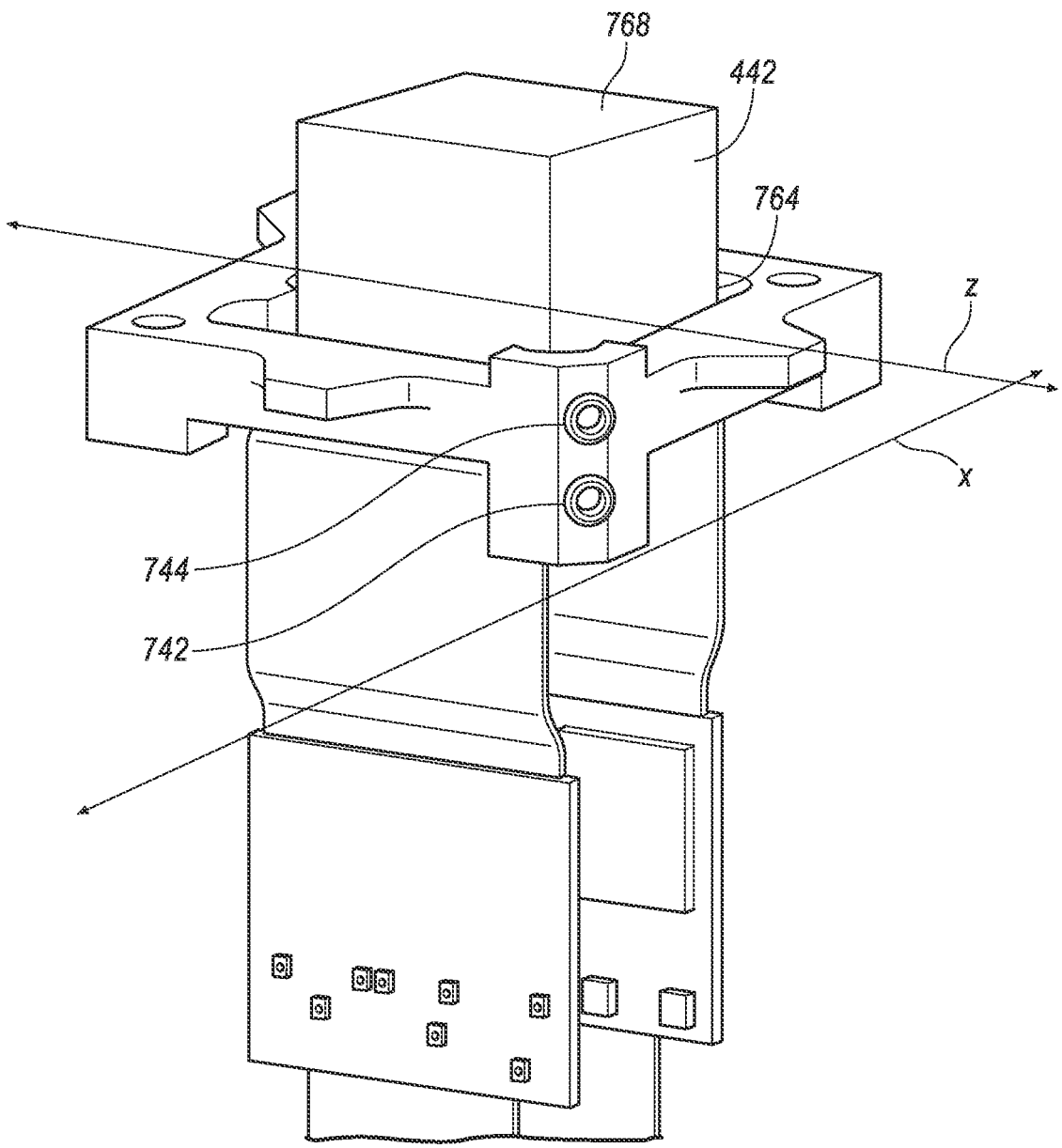
FIG. 12 shows the assembly of FIG. 11 with an anti-scatter grid positioned thereon.

FIG. 11 illustrates flex, (or "PCB" assembly for "printed circuit board") circuit 408 positioned within aperture 714 of intermediate block 712, but shown without lower block 704 or mount block 702, for illustrative purposes, to show their relative positions with one another. An underside 726 of intermediate block 712 includes, in one example, holes 772 that pass to lower surfaces or landings 730 that match with holes 734 that are at the corners of lower block 704, as seen in FIGS. 8 and 9. As seen in FIGS. 8 and 9, the holes and nubs are generally placed within the same plane of one another, except that one of the corners, corner 736 in this example, is at a different elevational location than the other three corners 738. Correspondingly, holes 772 of intermediate block 712 are likewise placed within a corresponding planar arrangement, with one of the corners 740 at a different planar location than the other three corners. In such fashion, when intermediate block 712 is placed on lower block 704, there is only one orientation between the two components 704, 712, serving as an obstruction or "poke yoke" that prevents the components from being assembled in an incorrect orientation with respect to one another. Having corner 740 of intermediate block 712 with additional depth, relative to the other corners thereof, provides for further ability to bias both flex circuit 408 and an anti-scatter grid (element 442 above) in both X and Z directions, as will be further discussed. That is, a depth 742 at corner 740 provides sufficient space or depth for both a first biasing device 742 and a second biasing device 744.

As seen in FIG. 11, first biasing device 742 is positioned at a depth or elevational location that corresponds with flex circuit 408, with second biasing device 744 positioned above an upper surface 746 of PCB or flex circuit 408. Thus, during assembly, when flex circuit 708 is positioned within aperture 714 of intermediate block 712 and on top of mount block 702 and lower block 704 (mount block 702 and lower block 704 are, again, not illustrated in FIGS. 11 and 12 for discussion purposes), then first biasing device 742 is used to bias flex circuit 708 in both X and Z directions at the same time, by pressing against a corresponding corner of flex circuit 408. Likewise, referring to FIG. 12, when anti-scatter grid 442 is positioned on upper surface 746 of flex circuit 408, then second biasing device 744 is used to bias anti-scatter grid 442 in both X and Z directions by pressing against a corresponding corner of anti-scatter grid 442. As such, in one example, one or both of the first and second biasing devices 742, 744, are set screws that may be each separately screwed against their respective component. In other examples, one or both of biasing devices 742, 744 may be spring-loaded devices that apply a spring force for biasing.

Further, and referring back to FIG. 9, mount block 702 is itself biased in both the X and Z directions according to the disclosure. An X-bias device 748 is used, in one example, by inserting a screw as X-bias device 748 into a threaded hole 750 that is visible in FIG. 8. A hole 752 in mount block 702, visible in FIG. 7, provides clearance for Z-bias device 748, when mount block 702 is positioned on top of Y-datum lower block upper surface 706 of lower block 704. Prior to screwing or tightening X-bias device 748, a Z-bias device 750 is also employed to provide a bias against mount block 702 when it is positioned in and on lower block 704. Z-bias device 750, in one example, is a spring loaded device that includes a spring-loaded end 754 that brings a pressure or force to bear against mount block 702. In one example, X-bias device 748 is a screw that may be any sort of screw such as a simple threaded screw or a shoulder screw.

Thus, during assembly, mount block 702 is positioned on lower block 704, and biased in both X and Z directions using Z-bias device 750 and X-bias device 748, such that Z-axis mount block planar surface 724 is aligned with and against Z-datum lower block surface 710, and such that X-axis mount block planar surface 722 is aligned with and against X-datum lower block surface 708. Likewise, an undersurface 756 of mount block 702 is positioned in contact with the Y-datum lower block upper surface 706 of lower block 704. In such fashion, mount block 702 is controllably positioned in 3-space and against the three reference surfaces of lower block 704.

Flex or PCB assembly 408 is positioned on top of mount block 702 when mount block is thus located. In one example, PCB assembly 408 is positioned on mount block 702, and then intermediate block 712 is positioned thereover. In another example, PCB assembly 408 is positioned within, and contained by, intermediate block 712 (using first biasing device 742), and then both are moved to positioned on mount block 702. Either way, according to the disclosure, by placing intermediate block 712 with respect to lower block 704 as described above, then PCB assembly 408 is thereby properly located with respect to mount block 702 when PCB assembly 408 is also biased in X and Z via first biasing device 742. PCB assembly 408 is also positioned in Y by placing its lower surface on top of surfaces 738, as well as that of a corresponding surface 707 of lower block 704. Once positioned thereon, and properly positioned in Y, cutouts 709 of intermediate block 712 thereby provide clearance so that manipulation of intermediate block 712 does not interfere negatively with PCB assembly 408. Similarly, anti-scatter grid 442 is likewise positioned on top of PCB assembly 408, and onto upper surface 746 thereof, and biased in both X and Z using second biasing device 744 against the respective surfaces in intermediate block 712, and also being positioned in Y off of the upper surface 746 of PCB assembly 408.

Thus, when the detector printed circuit board (PCB) assembly 408 is positioned in aperture 714, PCB assembly 408 is biased having an X-axis PCB assembly surface 758 aligned with the X-datum intermediate block surface 718, and having a Z-axis PCB assembly surface 760 aligned with the Z-datum intermediate block surface 720. The Y-dimension of all components are controlled in a very accurate fashion, as well.

Referring now to FIG. 13, an upper block 762. Also, when anti-scatter grid 400 is positioned on upper surface of the PCB assembly 746, an X-axis anti-scatter grid surface 764 is aligned with X-datum intermediate block surface 718 and a Z-axis anti-scatter grid surface 766 is aligned with Z-datum intermediate block surface 720. Upper block 762 engages with intermediate block 712 to position upper block 762 with respect to intermediate block 712 via holes as illustrated, with holes 764 aligning with holes 772. Thus, pair of holes 764 likewise engage are available for joining together a full assembly, as described with respect to FIG. 14.

Upper block includes an upper block Y-axis planar surface 766 such that, when upper block 762 is engaged with intermediate block 712, upper block Y-axis planar surface 766 contacts with a Y-axis surface 768 of anti-scatter grid 442. Upper block 762 further includes one of a flexible material and a spring-loaded element 768 that allow axial compliance or compression in the Y-axis, such that a positive pressure is exerted against Y-axis planar surface 768 of anti-scatter grid 442 from upper block Y-axis planar surface 766.

Referring now to FIG. 14, a full assembly of the assembled module is illustrated within the disclosed assembly fixture. Mini-module 400 is illustrated as being contained within lower block 704, intermediate block 712, and upper block 762. In one example, the three blocks 704, 712, and 762 are joined via a bolts or other threaded devices 770. In this example, bolts 770 pass through holes 764 of upper block 762, through holes 772 in intermediate block 712, and into holes 734 in lower block 704, with holes 734 threaded to receive bolts 770. Thus, during assembly, when glue or adhesive is applied between components of mini-module 400, the parts are all held tightly in place and in their proper 3-space locations, as defined by the various X, Y, and Z references surfaces (against which various edges or surfaces are biased), during curing of the adhesive.

Further, FIG. 14 illustrates the different leg lengths of the various components that provide for a poke yoke-type arrangement (to avoid assembling components in an incorrect orientation). For instance, as described above, intermediate block 712 includes a length of its legs at three of its corners, corresponding with corners 738 of lower block 704, and a different length corresponding with corner 736 of lower block 704. Thus, a leg 773 is longer than the other three legs 774 (two visible). Likewise, a leg 776 of upper block 762 is shorter than the other three legs 778 of upper block 762 (two visible). In such fashion, it is not possible to install intermediate block 712 onto lower block 704 if not set up so that leg 773 is positioned as shown, and it is also not possible to install upper block 762 onto intermediate block 712 if not set up so that leg 776 is positioned in line with leg 773 as shown.

Thus, according to the disclosure, the disclosed fixture first aligns the mount block and flex circuit in X and Z with space purposefully left between them. After the fixture is fully assembled, with the flexible material of the upper block applying force, the fixture releases the flex circuit, allowing the applied force to locate it and the anti-scatter grid properly in Y as well. This allows the parts to be mated with adhesive without risk of smearing the adhesive in X or Z.

According to the disclosure, a method of fabricating a detector mini-module to control component positioning in 3-space coordinates along an X-axis, a Y-axis, and a Z-axis, including obtaining a lower block that includes a Y-datum lower block upper surface, an X-datum lower block surface that is orthogonal to the Y-datum lower block upper surface, and a Z-datum lower block surface that is orthogonal to both the Y-datum lower block upper surface and the X-datum lower block surface, positioning a mount block for a detector in contact with the X-datum lower block surface, the Y-datum lower block upper surface, and the Z-datum lower block surface, and positioning an intermediate block on the lower block having, the intermediate block having an aperture passing through an upper surface and having an X-datum intermediate block surface and a Z-datum intermediate block surface. When a mount block for the detector mini-module is positioned on the lower block, the mount block is biased having an X-axis mount block planar surface aligned with the X-datum lower block surface, and biased having a Z-axis mount block planar surface aligned with the Z-datum lower block surface.

The disclosed method further includes biasing the PCB assembly by having an X-axis PCB assembly surface aligned with the X-datum intermediate block surface, and having a Z-axis PCB assembly surface aligned with the Z-datum intermediate block surface, and positioning an anti-scatter grid on an upper surface of the PCB assembly such that an X-axis anti-scatter grid surface is aligned with the X-datum intermediate block surface and a Z-axis anti-scatter grid surface is aligned with the Z-datum intermediate block surface.

The disclosed method further includes engaging an upper block with the intermediate block to position the upper block with respect to the intermediate block, the upper block having an upper block Y-axis planar surface that, when the upper block is engaged with the intermediate block, the upper block Y-axis planar surface contacts with a Y-axis surface of the anti-scatter grid. The upper block further includes one of a flexible material and a spring-loaded element that allow axial compliance or compression in the Y-axis, the method further comprising exerting a positive pressure against the Y-axis surface of the anti-scatter grid from the upper block Y-axis planar surface.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A fixture for fabricating a detector mini-module to control component positioning in 3-space coordinates along an X-axis, a Y-axis, and a Z-axis, comprising:
    a lower block comprising:
        a Y-datum lower block upper surface;
        an X-datum lower block surface that is orthogonal to the Y-datum lower block upper surface; and
        a Z-datum lower block surface that is orthogonal to both the Y-datum lower block upper surface and the X-datum lower block surface, wherein a mount block for a detector is positionable and in contact with the X-datum lower block surface, the Y-datum lower block upper surface, and the Z-datum lower block surface; and
    an intermediate block positionable on the lower block having an aperture passing through an upper surface and having an X-datum intermediate block surface and a Z-datum intermediate block surface;
    wherein, when a mount block for the detector mini-module is positioned on the lower block, the mount block is biased having an X-axis mount block planar surface aligned with the X-datum lower block surface, and biased having a Z-axis mount block planar surface aligned with the Z-datum lower block surface.

2. The fixture according to claim 1, wherein, when a detector printed circuit board (PCB) assembly is positioned in the aperture, the PCB assembly is biased having an X-axis PCB assembly surface aligned with the X-datum intermediate block surface, and having a Z-axis PCB assembly surface aligned with the Z-datum intermediate block surface.

3. The fixture according to claim 2, wherein, when an anti-scatter grid is positioned on an upper surface of the PCB assembly, an X-axis anti-scatter grid surface is aligned with the X-datum intermediate block surface and a Z-axis anti-scatter grid surface is aligned with the Z-datum intermediate block surface.

4. The fixture according to claim 3, further comprising an upper block that engages with the intermediate block to position the upper block with respect to the intermediate block, the upper block having an upper block Y-axis planar surface that, when the upper block is engaged with the intermediate block, the upper block Y-axis planar surface contacts with a Y-axis surface of the anti-scatter grid.

5. The fixture according to claim 4, wherein the upper block further comprises one of a flexible material and a spring-loaded element that allow axial compliance or compression in the Y-axis, such that a positive pressure is exerted against the Y-axis surface of the anti-scatter grid from the upper block Y-axis planar surface.

6. The fixture according to claim 5, wherein the spring-loaded element is a planar bearing.

7. The fixture according to claim 4, wherein at least one of the mount block, the anti-scatter grid, and the PCB assembly is biased in both X and Z directions using a bias pressure device positioned in a corner of the lower block.

8. The fixture according to claim 1, wherein the mount block is L-shaped, having a portion of the L-shape extending along the Y-axis, and the mount block is biased having the X-axis mount block planar surface positioned against the X-datum lower block surface using a fastener passing through an aperture in the portion of the lower block.

9. The fixture according to claim 8, wherein the fastener is a screw.

10. A method of fabricating a detector mini-module to control component positioning in 3-space coordinates along an X-axis, a Y-axis, and a Z-axis, comprising:
    obtaining a lower block that includes a Y-datum lower block upper surface, an X-datum lower block surface that is orthogonal to the Y-datum lower block upper surface, and a Z-datum lower block surface that is orthogonal to both the Y-datum lower block upper surface and the X-datum lower block surface;
    positioning a mount block for a detector in contact with the X-datum lower block surface, the Y-datum lower block upper surface, and the Z-datum lower block surface; and
    positioning an intermediate block on the lower block having, the intermediate block having an aperture passing through an upper surface and having an X-datum intermediate block surface and a Z-datum intermediate block surface;
    wherein, when a mount block for the detector mini-module is positioned on the lower block, the mount block is biased having an X-axis mount block planar surface aligned with the X-datum lower block surface, and biased having a Z-axis mount block planar surface aligned with the Z-datum lower block surface.

11. The method according to claim 10, further comprising:
    positioning a detector printed circuit board (PCB) assembly in the aperture; and
    biasing the PCB assembly by having an X-axis PCB assembly surface aligned with the X-datum intermediate block surface, and having a Z-axis PCB assembly surface aligned with the Z-datum intermediate block surface.

12. The method according to claim 11, further comprising positioning an anti-scatter grid on an upper surface of the PCB assembly such that an X-axis anti-scatter grid surface is aligned with the X-datum intermediate block surface and a Z-axis anti-scatter grid surface is aligned with the Z-datum intermediate block surface.

13. The method according to claim 12, further comprising engaging an upper block with the intermediate block to position the upper block with respect to the intermediate block, the upper block having an upper block Y-axis planar surface that, when the upper block is engaged with the intermediate block, the upper block Y-axis planar surface contacts with a Y-axis surface of the anti-scatter grid.

14. The method according to claim 13, wherein the upper block further comprises one of a flexible material and a spring-loaded element that allow axial compliance or compression in the Y-axis, the method further comprising exerting a positive pressure against the Y-axis surface of the anti-scatter grid from the upper block Y-axis planar surface.

15. The method according to claim 14, wherein the spring-loaded element is a planar bearing.

16. The method according to claim 13, further comprising biasing at least one of the mount block, the anti-scatter grid, and the PCB assembly in both X and Z directions using a bias pressure device positioned in a corner of the lower block.

17. The method according to claim 10, wherein the mount block is L-shaped, having a portion of the L-shape extending along the Y-axis, the method further comprising biasing the mount block having the X-axis mount block planar surface positioned against the X-datum lower block surface using a fastener passing through an aperture in the portion of the lower block.

18. The fixture according to claim 17, wherein the fastener is a screw.

* * * * *